US012782184B2

(12) United States Patent
Golitz et al.

(10) Patent No.: US 12,782,184 B2

(45) Date of Patent: Nov. 3, 2026

(54) PROCESS WATER ANALYZER

(71) Applicant: HACH LANGE GMBH, Berlin (DE)

(72) Inventors: Andreas Golitz, Berlin (DE); Manfred Battefeld, Berlin (DE); Bas De Heij, Berlin (DE); Maik Heuwold, Berlin (DE); Sebastian Minke, Berlin (DE)

(73) Assignee: HACH LANGE GMBH, Berlin (DE)

( * ) Notice: Subject to any disclaimer, the term of this patent is extended or adjusted under 35 U.S.C. 154(b) by 84 days.

(21) Appl. No.: 18/995,639

(22) PCT Filed: Jul. 11, 2023

(86) PCT No.: PCT/EP2023/069190

§ 371 (c)(1),
(2) Date: Jan. 16, 2025

(87) PCT Pub. No.: WO2024/017711

PCT Pub. Date: Jan. 25, 2024

(65) Prior Publication Data

US 2026/0022960 A1 Jan. 22, 2026

(30) Foreign Application Priority Data

Jul. 18, 2022 (EP) .................................... 22185435

(51) Int. Cl.

*G01F 11/02* (2006.01)
*G01N 33/18* (2006.01)

(52) U.S. Cl.

CPC ........... *G01F 11/029* (2013.01); *G01N 33/18* (2013.01)

(58) Field of Classification Search

CPC ........ G01F 11/029; G01F 22/02; F04B 13/00; F04B 17/03; F04B 49/065; F04B 2205/09;

(Continued)

(56) References Cited

U.S. PATENT DOCUMENTS

2011/0318242 A1 12/2011 Nay
2012/0167673 A1* 7/2012 Farjam ................ B01L 3/50273 73/64.56

(Continued)

OTHER PUBLICATIONS

European Patent Office, International Search Report and Written Opinion, Oct. 18, 2023, 10 pages, European Patent Office. PCT/EP2023/069190.

*Primary Examiner* — David J Walczak

(74) *Attorney, Agent, or Firm* — Ference & Associates LLC

(57) ABSTRACT

A process water analyzer for automatically analyzing a water sample, including a process liquid reservoir tank with a process liquid defining a reservoir liquid level at a reservoir liquid level height, a dosage chamber fluidically connected to and positioned downstream of the process liquid reservoir tank, and a positive displacement dosage pump for sucking process liquid into the dosage chamber, whereas an air cushion is always provided vertically between the dosage pump and the dosage chamber liquid level so that a liquid column with an effective vertical liquid column length exists between the reservoir liquid level and the dosage chamber liquid level, whereas the dosage pump sucks a pressure-adapted gas volume of the air cushion, and whereas a process liquid dosage control unit provides the value of the pressure-adapted pumped gas volume dependent on the air cushion pressure effected by the effective vertical liquid column length.

8 Claims, 1 Drawing Sheet

(58) Field of Classification Search
CPC .... G01N 33/18; G01N 35/00584; G01N 1/14; G01N 33/1846; G01N 21/78; G01N 35/10; G01N 33/182; G01N 33/1826
USPC .................................. 222/52, 55, 56, 59, 61
See application file for complete search history.

(56) References Cited

U.S. PATENT DOCUMENTS

| | | | | |
|---|---|---|---|---|
| 2019/0151768 | A1 | 5/2019 | Uthemann et al. | |
| 2020/0225130 | A1* | 7/2020 | von Hirtz ............ | G01N 1/2247 |

* cited by examiner

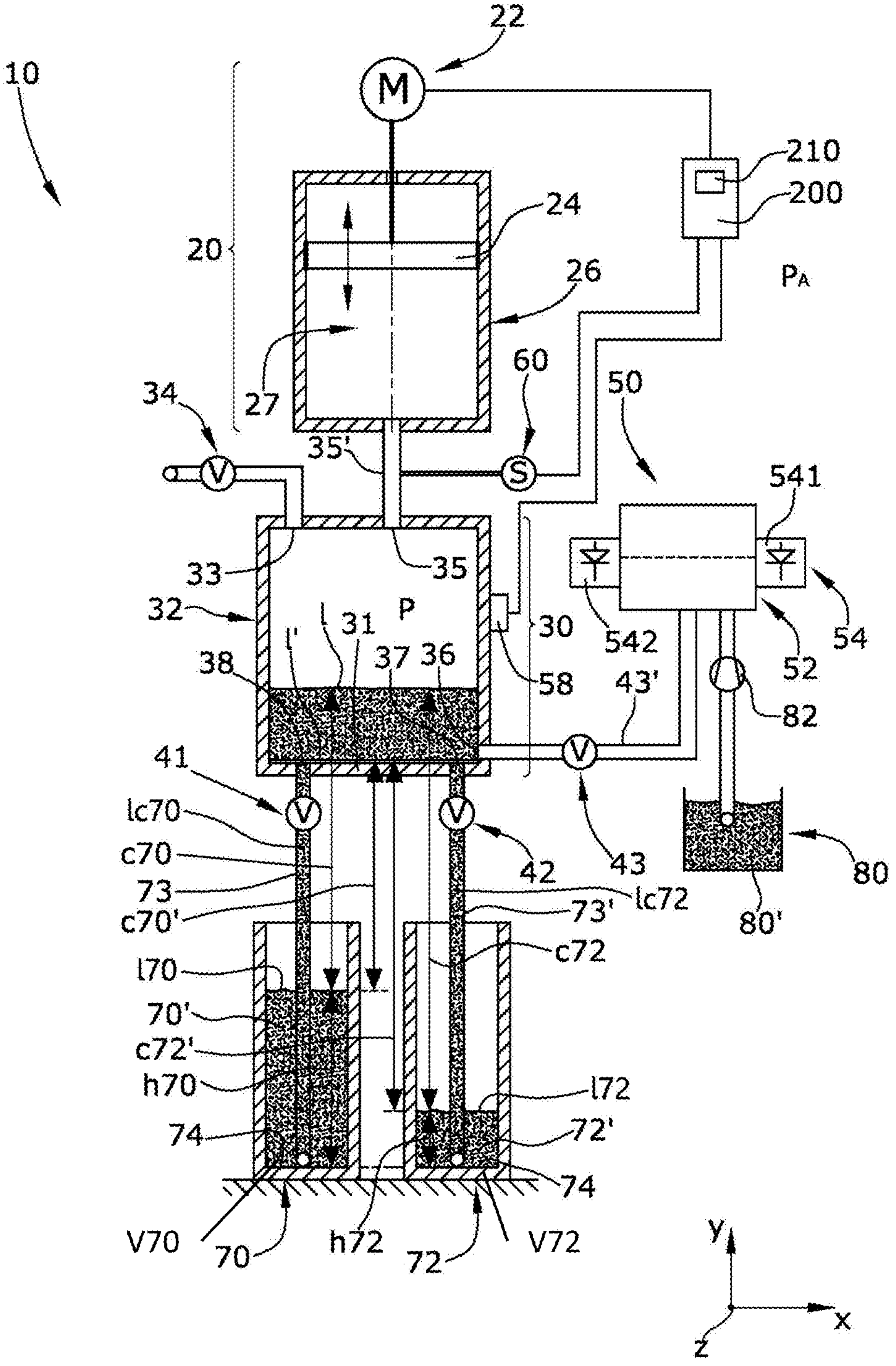
10
22
M
210
200
20
24
26
PA
27
60
50
34
V
35'
S
541
33
35
32
P
30
542
54
l'
l
31
37
36
38
58
43'
52
82
41
V
lc70
V
c70
42
43
80
73
lc72
c70'
73'
80'
c72
l70
70'
c72'
h70
l72
74
72'
74
V70
70
h72
72
V72
y
x
z

PROCESS WATER ANALYZER

The invention is directed to a process water analyzer for automatically analyzing a parameter of a water sample.

A process water analyzer quasi-continuously determines a parameter of water. The parameter can be an analyte as, for example, the concentration of a substance, for example of ammonium or phosphate, or can be a more complex parameter as, for example, the total organic carbon (TOC). A process water analyzer comprises one or more process liquid reservoir tanks with process liquids which are necessary to provide the complete measurement process. Typical process liquids are reagents for providing a reaction with the analyte, for example a colour reaction, or are other process liquids, such as a cleaning liquid or a standard solution liquid.

The process liquid is stored in a process liquid reservoir tank filled with the process liquid. The process liquid reservoir volume in the reservoir tank defines a reservoir liquid level at a reservoir liquid level height.

A dosage chamber is provided which is fluidically connected to the process liquid reservoir tank and is provided fluidically downstream of the process liquid reservoir tank and upstream of a measurement chamber of an analyzer unit where the final quantitative measurement of the parameter is provided, for example by a photometric device.

For a precise dosage of the process liquid, a process water analyzer typically is provided with a very precise positive displacement dosage pump which allows to first suck a set process liquid volume of the process liquid from the process liquid reservoir tank into the separate dosage chamber, and then to push the set process liquid volume from the dosage chamber to an analyzer unit, for example to a photometer.

An air cushion is always provided vertically between the dosage pump and the dosage chamber process liquid level to avoid any direct contact of the process liquid with the dosage pump. This measure avoids any contamination of the dosage pump with any of the process liquids and thereby guarantees a long lifetime of the dosage pump.

A hydrostatically relevant liquid column with an effective vertical liquid column length is always provided between the reservoir liquid level of the process liquid and the dosage chamber liquid level of the same process liquid. The higher the effective vertical liquid column length is, the more is the air cushion expanded by the weight of the liquid column hanging directly below the air cushion during the dosage pumping process step. The vertical liquid column length depends on the reservoir liquid level of the process liquid in the reservoir tank.

For directly detecting the reservoir liquid level, several filling level sensors would be necessary for all process liquid reservoir tanks, which is expensive. It is therefore preferred to provide no filling level sensors for any of the reservoir tanks. As a consequence, the vertical liquid column length between the dosage chamber liquid level and the reservoir liquid level is not known precisely, so that the expanding effect of the vertical liquid column for the air cushion between the dosage chamber liquid level and the dosage pump is not known. As a result, it is not possible to pump the exact set process liquid volume into the dosage chamber. The resulting inaccuracy of the pumped process liquid volume is in the range of a few percent which makes it necessary to always pump a worst case volume of the process liquid so that, in most cases, more process liquid is consumed than necessary. If the analyzer unit of the process water analyzer is a photometer, the systematic overdosage of the process liquid volume can cause a systematic photometric fault caused by the inherent colour of the process liquid.

It is an object of the invention to provide a process water analyzer with an improved accuracy for pumping a set process liquid volume from a process liquid reservoir tank to the dosage chamber.

This object is solved with a process water analyzer with the features of main claim 1.

The process water analyzer according to the invention for automatically analyzing a parameter of a water sample comprises at least one process liquid reservoir tank with a process liquid, for example a colorimetric reagent, a cleaning liquid, a rinsing liquid and/or one or more standard solution liquid. The process liquid reservoir volume defines a reservoir liquid level at a reservoir liquid level height which is the vertical distance between the bottom of the reservoir tank and the level of the process liquid surface within the reservoir tank. The process liquid reservoir tank preferably is a disposable tank.

The process water analyzer is provided with a dosage chamber fluidically connected to the process liquid reservoir tank and being positioned fluidically downstream of the process liquid reservoir tank. The dosage chamber preferably is positioned vertically higher than the process liquid reservoir tank. The dosage chamber is a separate chamber which is used for precisely dosing the volume of the liquid sample and of the process liquids before defined volume of the liquid is pumped to an analyzing unit.

The process water analyzer is provided with a positive displacement dosage pump fluidically connected to the top of the dosage chamber for sucking a defined set process liquid volume from the corresponding process liquid reservoir tank into the dosage chamber via a liquid line having an inlet opening in the bottom region of the process liquid reservoir tank and having the liquid line outlet opening at the bottom of the dosage chamber. An air cushion is always provided vertically between the dosage pump and the dosage chamber process liquid level to avoid any direct contact of the dosage pump with the process liquid. This measure avoids any contamination of the dosage pump with any of the process liquids and thereby guarantees a long lifetime of the dosage pump.

If the process liquid reservoir tank is arranged vertically below the dosage chamber, a liquid column with an effective vertical liquid column length is hanging vertically below the air cushion and thereby expands the total volume of the air cushion so that the static gas pressure in the closed air cushion is reduced accordingly. The effective vertical liquid column length is the vertical distance between the dosage chamber liquid level in the dosage chamber and the reservoir liquid level in the reservoir tank. The reservoir liquid level has a total reservoir level height above the reservoir tank bottom wall.

The process water analyzer is provided with a process liquid dosage control unit which provides the value of a pressure-adapted pumped gas volume which pressure-adapted pumped gas volume depends on the air cushion pressure effected by the effective vertical liquid column length, the specific weight of the process liquid and the liquid level surface area of the process liquid in the dosage chamber. According to the invention, the dosage pump directly sucks the pressure-adapted pumped gas volume of the air cushion having an air cushion pressure so that the exact set process liquid volume is indirectly pumped into the dosage chamber. The gas volume expanding effect of the varying vertical liquid column is thereby compensated so that the accuracy of the process liquid volume pumped into the dosage chamber does not depend on the effective vertical liquid column length anymore.

As a consequence, no general offset volume of the process liquid needs to be pumped anymore so that the consumption of the process liquid is reduced accordingly. In photometric applications, a systematic fault caused by the inherent colour of the process liquid is not given anymore.

According to a preferred embodiment of the invention, the process water analyzer is provided with a gas pressure sensor fluidically connected to the dosage pump inlet/outlet opening for directly detecting and sensing the gas pressure of the air cushion above the dosage chamber liquid surface. Preferably, the gas pressure sensor is fluidically provided in the top region of the dosage chamber or between the dosage chamber and the dosage pump. Since the gas pressure of the air cushion is directly determined by the gas pressure sensor, the resulting total volume of the air cushion being substantially proportional to the gas pressure can directly be calculated, so that finally the value of the pressure-adapted pumped gas volume can be calculated.

Preferably, the process liquid dosage control unit also determines the actual reservoir liquid level on the basis of the air cushion pressure provided by the gas pressure sensor.

According to an alternative embodiment of the invention, a reservoir liquid level register for providing the actual reservoir liquid level is provided. The process liquid dosage control unit provides the pressure-adapted pumped gas volume dependent on the effective vertical liquid column length which depends on the actual reservoir liquid level provided by the reservoir liquid level register. Generally, the reservoir liquid level register can work in different ways, but preferably records and accumulates the dosage pump activities for pumping of the process liquid to thereby calculate the reservoir liquid level of the process liquid in the reservoir tank. Since the actual reservoir liquid level is known from the reservoir liquid level register, the effective vertical liquid column length is known, as well, so that the value of the pressure-adapted pumped gas volume can be calculated.

Preferably, the dosage chamber and/or any of the liquid reservoir tanks is/are provided without any continuous liquid level sensor which could determine the actual level of the liquid in the dosage chamber or in the liquid reservoir tanks.

Preferably, the dosage pump is a piston pump. The piston pump pumps the fluid very precisely and with a high constancy.

Preferably, the dosage pump is provided with an electric step motor. The electric step motor in the context of the present invention is every motor which allows to precisely control and record the number of motor rotor rotation steps.

Preferably, the gas pressure sensor is a differential gas pressure sensor measuring the pressure difference of the gas pressure in relation to the atmospheric pressure of the direct process water analyzer environment. The differential gas pressure sensor compensates effects resulting from any deviation of the actual environmental atmospheric pressure from a standard pressure of, for example, 1013 mbar. Using a differential gas pressure sensor therefore makes a precise determination of the actual atmospheric pressure of the water analyzer environment redundant.

Preferably, a total atmospheric pressure sensor can be provided to determine the total atmospheric pressure as a reference.

One embodiment of the invention is explained with reference to the enclosed drawing.

The FIGURE schematically shows a process water analyzer according to the invention with a process liquid dosage control unit using a gas pressure sensor for providing the value of the pressure-adapted pumped gas volume to precisely pump a set process liquid volume into a dosage chamber.

The FIG. 1 schematically shows a process water analyzer 10 for automatically analyzing a parameter of a water sample coming from a wastewater plant basin 80 filled with wastewater 80'. The analyzer 10 is provided with a photometer 50 photometrically analyzing and determining the concentration of a parameter of the water sample pumped by a sample pump 82 from the wastewater basin 80 to a photometric measurement chamber 52 of the photometer 50. The photometric measurement chamber 52 is provided with a photometric unit 54 comprising a photometric light source 541 and a photometric receiver 542. Generally, the measurement chamber can be a part of another type of an analyzer measurement unit.

In the FIGURE, the vertical direction is y, and the horizontal plane is defined by x and z.

The process water analyzer 10 also comprises two process liquid reservoir tanks 70, 72 with process liquids 70', 72', a dosage chamber 30 fluidically connected to the process liquid reservoir tanks 70, 72 by a vertical supply line 73, 73', respectively, and a positive displacement dosage pump 20. However, six or even more different process liquid reservoir tanks could be provided.

The process liquids 70', 72' are, in this embodiment, a reagent liquid and a cleaning liquid. The reagent liquid can be a reagent for the colorimetric determination of, for example, phosphate. The actual process liquid reservoir volumes V70 and V72 in the corresponding reservoir tank 70,72 result in a reservoir liquid level l70, l72 having a reservoir level height h70, h72 above the bottom wall surface 74 of the corresponding reservoir tanks 70, 72. A typical total liquid volume of a new and completely filled process liquid reservoir tank is, for example, 2.0 liter.

The dosage chamber 30 having a typical volume of 3.6 ml is located vertically higher than the process liquid reservoir tanks 70, 72 and is fluidically connected to the process liquid reservoir tanks 70, 72 via two process liquid inlet openings 37,38 at the horizontal bottom wall 31 of the dosage chamber housing 32. The process liquid inlet openings 37, 38 define the vertical top end of the supply lines 73, 73', respectively. The vertical downward end of the supply lines 73, 73' is provided close to the bottom wall surface 74 of the corresponding reservoir tank 70, 72. A switchable supply line valve 41, 42 is provided in the course of every supply line 73, 73'.

At the top wall of the dosage chamber 30, a venting opening 33 is provided which allows a venting of the dosage chamber interior with atmospheric pressure PA if a switchable venting valve 34 is open. A pump line opening 35 is provided at the top wall of the dosage chamber 30. The interior of the dosage chamber 30 is fluidically connected to the dosage pump 20 via the pump line opening 35 and a pump line 35'. A differential gas pressure sensor 60 is provided at the pump line 35'. The dosage chamber 30 is provided with an optical one-point liquid level sensor 58 which detects the absence or the presence of a liquid at the vertical level of the liquid level sensor 58.

The dosage chamber 30 is also provided with an analyzer liquid outlet opening 36 fluidically connecting the dosage chamber interior via a connection line 43' and a switchable photometer line valve 43 with the photometer measurement chamber 52. After a photometric measurement has been provided, the liquid of the photometer measurement chamber 52 is drained into a waste liquid container.

The positive displacement dosage pump 20 is provided with an electric pump motor 22 which is an electric step motor and which actuates a pump piston 24 linearly moving within a pump cylinder 26. The total displacement of the dosage pump 20 is 5.0 ml and the total number of motor steps for actuating the piston 24 from one cylinder end to the other cylinder end is 5000 steps.

An air cushion 27 is provided and located fluidically between the pump piston 24 of the dosage pump 20 and the actual dosage chamber liquid level l of the liquid in the dosage chamber 30. The gas pressure sensor 60 is a differential sensor measuring the pressure difference between the gas pressure P of the air cushion 27 and the atmospheric pressure PA of the environment of the analyzer 10.

The process water analyzer 10 comprises a process liquid dosage control unit 200 which is provided with a reservoir liquid level register 210 and which controls all pumping actions and motor steps of the dosage pump 20. The process liquid dosage control unit 200 receives the pressure signal of the gas pressure sensor 60 and a liquid presence indication signal of the liquid level sensor 58. The process liquid dosage control unit 200 also controls the photometer 50, the sample pump 82, and all switchable valves 34, 41, 42, 43.

After two new and completely filled process liquid reservoir tanks 70, 72 have been applied to the water process water analyzer 10, an initial automatic reference measurement is provided which is controlled by the process liquid dosage control unit 200 to verify if the new process liquid reservoir tanks 70, 72 is/are completely filled with the correct process liquid. The initial reference measurement is controlled by the process liquid dosage control unit 200:

The first supply line valve 41 is opened, and the second supply line valve 42, the photometer line valve 43 and the venting valve 34 are closed. The dosage pump 20 sucks a predefined priming volume Vprime of the first process liquid 70' through the corresponding supply line 73 into the dosage chamber 30. The value of the priming volume Vprime is sufficiently large to guarantee that the priming liquid upper level is definitely right above the liquid outlet opening 36.

Then, the first supply line valve 41 is closed, the second supply line valve 42 remains closed and the photometer line valve 43 is opened, so that the process liquid in the dosage chamber 30 is pumped by the activated dosage pump 20 through the liquid outlet opening 36 to the photometer 50. The liquid in the dosage chamber 30 falls to a liquid column reference level l' where the liquid level remains. This liquid column reference level l' preferably is precisely in the horizontal plane defined by the liquid inlet openings 37, 38.

In the next reference process step, the photometer line valve 43 is closed and the venting valve 34 is shortly opened and then closed again to have the atmospheric pressure PA of the environment as a defined reference dosage chamber pressure P within the dosage chamber 30.

Then, the first supply line valve 41 is opened, and the other three valves 34, 42, 43 remain closed so that a vertical liquid column lc70, lc72 between the liquid column reference level l' and the reservoir liquid level l70 expands the air cushion 27 so that the air cushion 27 has a total gas pressure P below the environmental atmospheric pressure PA.

The specific weight of the process liquid 70' is known and has been memorized in the process liquid dosage control unit 200 so that the dosage control unit 200 can determine or calculate from the pressure P the total vertical liquid column length c70', determines from the liquid column length c70' the precise reservoir liquid level l70, and finally determines from the reservoir liquid level l70 the actual process liquid reservoir volume V70 of the new process liquid reservoir tank 70.

The same procedure is applied accordingly for the other new liquid reservoir tank 72, so that the process liquid dosage control unit 200 determines the liquid column length c72' and the resulting liquid process liquid reservoir volume V72 of the second liquid reservoir tank 72.

The reservoir liquid level register 210 records all pumping actions and pump motor steps of the dosage pump 20 sucking one of the process liquids 70', 72' from the process liquid reservoir tanks 70, 72 through the dosage chamber 30, and continuously sums up the consumed volumes of the process liquid 70', 72' so that the remaining actual process liquid reservoir volumes V70, V72 can always be roughly calculated.

Additionally, from time to time, a plausibility measurement can be provided by the process liquid dosage control unit 200 to verify and, if necessary, to correct the calculated actual process liquid reservoir volumes V70, V72 and the corresponding vertical reservoir liquid levels l70, l72 memorized in the reservoir liquid level register 210. In a plausibility measurement, the pressure P caused by the liquid column lc70, lc72 of one of the process liquids 70', 72' is measured by the pressure sensor 60 and is checked for plausibility with the roughly calculated dosage chamber liquid level I and the roughly calculated reservoir liquid level l70 memorized in the reservoir liquid level register 210.

As described above, the reservoir liquid level register 210 always roughly knows the actual reservoir liquid levels l70, l72. For a measurement action, the process liquid dosage control unit 200 causes the dosage pump 22 to pump and suck a pressure-adapted gas volume Vgas of the air cushion 27 so that a set process liquid volume Vliquid is pumped from the corresponding process liquid reservoir tank 70, 72 into the dosage chamber 30.

Before the pumping action is started, the process liquid dosage control unit 200 determines the actual effective vertical liquid column length c70, c72 based on the actual reservoir liquid levels l70, l72, and calculates the value of the pressure-adapted pumped gas volume Vgas dependent on the expected air cushion pressure P effected by the effective vertical liquid column length c70, c72, the surface area of the liquid having the dosage chamber liquid level and the corresponding specific weight of the process liquid 70', 72'. As a result, the gas volume expanding effect of the vertical liquid column lc70, lc72 is compensated so that the pumped and sucked set process liquid volume Vliquid is not affected by the actual reservoir liquid level l70, l72.

The adaption and calculation of the pressure-adapted gas volume Vgas can simply be based on the air cushion pressure P continuously controlled by the gas pressure sensor 60. The process liquid dosage control unit 200 calculates the pressure-adapted gas volume Vgas for pumping the set process liquid volume Vliquid on the basis of the air cushion pressure P, the liquid surface area and the specific weight of the process liquid 70', 72'.

After the set process liquid volume Vliquid has precisely being pumped into the dosage chamber 30 up to a set process liquid chamber level l, the process liquid dosage control unit 200 switches the valves 34, 41, 42, 43 accordingly and causes the dosage pump 20 to push the complete liquid volume having the set process liquid volume Vliquid from the dosage chamber 32 to the photometric measurement chamber 52 of the photometer 50.

The invention claimed is:

1. A process water analyzer for automatically analyzing a parameter of a water sample, comprising:

a process liquid reservoir tank with a process liquid, whereas a process liquid reservoir volume in the reservoir tank defines a reservoir liquid level at a reservoir liquid level height;

a dosage chamber fluidically connected to the process liquid reservoir tank and being positioned fluidically downstream of the process liquid reservoir tank; and a positive displacement dosage pump fluidically connected to a top of the dosage chamber for sucking in the process liquid into the dosage chamber;

whereas an air cushion is always provided vertically between the dosage pump and a dosage chamber liquid level in the dosage chamber, so that a liquid column with an effective vertical liquid column length is given between the reservoir liquid level and the dosage chamber liquid level;

whereas the dosage pump directly sucks a pressure-adapted gas volume of the air cushion having an air cushion pressure so that a set process liquid volume is pumped into the dosage chamber; and whereas a process liquid dosage control unit is provided, the process liquid dosage control unit providing a value of the pressure-adapted gas volume dependent on the air cushion pressure effected by the liquid column with the effective vertical liquid column length.

2. The process water analyzer of claim 1, whereas a gas pressure sensor is provided for directly sensing the air cushion pressure.

3. The process water analyzer of claim 2, whereas the process liquid dosage control unit determines an actual reservoir liquid level on a basis of the air cushion pressure provided by the gas pressure sensor.

4. The process water analyzer of claim 3, wherein the gas pressure sensor is a differential sensor measuring a pressure difference of a gas pressure to an atmospheric pressure.

5. The process water analyzer of claim 1, wherein the liquid reservoir tank is provided free of a liquid level sensor.

6. The process water analyzer of claim 1, wherein the dosage pump is a piston pump.

7. The process water analyzer of claim 1, wherein the dosage pump is provided with an electric step motor.

8. The process water analyzer of claim 1, comprising a reservoir liquid level register for providing an actual reservoir liquid level, whereas the process liquid dosage control unit provides the pressure-adapted gas volume dependent on the effective vertical liquid column length dependent on the actual reservoir liquid level provided by the reservoir liquid level register.

* * * * *